United States Patent
Wynne et al.

(10) Patent No.: US 6,686,494 B1
(45) Date of Patent: Feb. 3, 2004

(54) SYNTHESIS OF S-ALKYL AND S-ARYL THIOCARBAMATES, ONE-POT TWO-STEP GENERAL SYNTHESIS

(75) Inventors: James W. Wynne, Alexandria, VA (US); Arthur W. Snow, Alexandria, VA (US)

(73) Assignee: The United States of America as represented by the Secretary of the Navy, Washington, DC (US)

( * ) Notice: Subject to any disclaimer, the term of this patent is extended or adjusted under 35 U.S.C. 154(b) by 0 days.

(21) Appl. No.: 10/384,928

(22) Filed: Mar. 6, 2003

(51) Int. Cl.$^7$ .................... C07C 315/00; C07C 317/00; C07C 229/00; C07C 333/00
(52) U.S. Cl. .................. 558/232; 562/555; 562/556; 562/27; 560/12; 560/132
(58) Field of Search ................................. 562/553, 555, 562/556, 27; 558/232; 560/12, 132

(56) References Cited

U.S. PATENT DOCUMENTS 3,582,314 A   6/1971   Konnai et al.

OTHER PUBLICATIONS

Maeda, DE–Pat. 1,817,662, Kumiai Chemical Industry Co., LTD., Chem. Abstr. 74, 12864 (1970).
Harold Kwart & E. Robert Evans, "The Vapor Phase Rearrangement of Thioncarbonates and Thioncarbamates," J. Org. Chem., 1966, 31, 410–413.
Melvin S. Newman & Harold A. Karnes, "The Conversion of Phenols to Thiophenols via Dialkylthiocarbamates," J. Org. Chem., 1966, 31, 3980–3984.
Melvin S. Newman & Frederick W. Hetzel, "Preparation of Olefins by Pyrolysis of O–Alkyl Dimethylthiocarbabmates," J. Org. Chem., 1969, 34, 3604–3606.
R. E. Hackler & T. W. Balko, "The [3,3]–Sigmatropic Rearrangement of Allylic Dialkylthiocarbamates," J. Org. Chem., 1973, 38, 2106–2109.
William D. Jones, Kelly A. Reynolds, Caroline K. Sperry, Rene J. Lachicotte, Stephen A. Godleski & Ronald R. Valente, "Selective Carbonylation Routes to Thiocarbamates. An Alternative to Phosgene," Organometallics, 2000, 19, 1661–1669.

Hitoshi Kuniyasu, Hiroshi Hiraike, Masaki Morita, Aoi Tanaka, Kunihiko Sugoh & Hideo Kurosawa, "Palladium–Catalyzed Azathiolation of Carbon Monoxide," J. Org. Chem., 1999, 64, 7305–7308.
Achim Bohme & Hans–Joachim Gais, "Palladium(O) catalyzed enantioselective rearrangement of O–allylic thiocarbamates to S–allylic thiocarbamates: asymmetric synthesis of allylic thiols," Tetrahedron: Asymmetry, 1999, 10, 2511–2514.
Josemon Jacob, Kelly A. Reynolds, William D. Jones, Stephen A. Godleski & Ronald R. Valente, "Nickel–Mediated Selective Carbonylation Routes to Thiocarbamates," Organometallics, 2001, 20, 1028–1031.
Robert A. Batey, Chiaki Yoshina–Ishii, Scott D. Taylor & V. Santhakumar,"A New Protocal for the Formation of Carbamates and Thiocarbamates using Carbamoyl Imidazolium Salts," Tetrahedron Lett., 1999, 40, 2669–2672.
T. Indrasena Reddy, B. M. Bhawal & S. Rajappa, "A Facile General Method for the Preparation of S–Methyl Thiolcarbamates using Zeolite Catalysts," Tetrahedron Lett., 1992, 33, 2857–2860.
M. Beji, H. Sbihi, A. Baklouti & A. Cambon, "Synthesis of F–alkyl N–sulfonyl carbomates and thiocarbamates," J. Fluorine Chem., 1999, 99, 17–24.
E. N. Zil'Berman & A. Ya. Lazaris, "The Reaction of Organic Thiocyanates with Water in Presence of Hydrogen Chloride," J. Gen. Chem. USSR, 1963, 33, 1012–1014.
Advanced Organic Chemistry 5th Ed., Michael B. Smith and Jerry March, Eds., Wiley Interscience: New York, 2001, Chapter 16.

Primary Examiner—Shailendra Kumar
Assistant Examiner—Karl Puttlitz
(74) Attorney, Agent, or Firm—John J. Karasek; Rebecca L. Forman

(57) ABSTRACT

A method for preparing S-alkyl and S-aryl thiocarbamates comprising reacting a precursor thiol reagent with trichloroacetyl chloride to produce an S-alkyl and S-aryl trichloroacetyl thioester intermediate, which is reacted with an amine to yield the corresponding thiocarbamate product. Also disclosed is the method for preparing S-alkyl and S-aryl thiocarbamates comprising reacting an amine with trichloroacetyl chloride to produce a trichloroacetamide intermediate, which is then reacted with the precursor thiol to yield the corresponding thiocarbamate product.

20 Claims, No Drawings

SYNTHESIS OF S-ALKYL AND S-ARYL THIOCARBAMATES, ONE-POT TWO-STEP GENERAL SYNTHESIS

BACKGROUND OF THE INVENTION

1. Field of the Invention

The present invention relates to thiocarbamates and, more specifically, to a synthetic method for preparing S-alkyl and S-aryl thiocarbamates.

2. Description of Related Art

The importance of S-alkyl and S-aryl thiocarbamate compounds as herbicides, pesticides and other biological applications has been recognized for many years. The basic S-alkyl and S-aryl thiocarbamate (S-alkylthiourethane) structure is as follows:

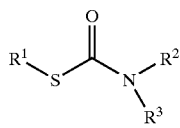

Such compounds have been of interest due to their numerous biological effects including anesthetic, fungicidal, bactericidal, pesticidal and antiviral activity. These compounds are most noted for their use as commercial herbicides and thus have received considerable attention in the literature. See Maeda, T., DE-Pat. 1817662, Kumiai Chemical Industry Co., LTD.; *Chem. Abstr.* 74, 12864 (1970); and U.S. Pat. No. 3,582,314 to Konnai et al., which are incorporated herein by reference. They have been used for control of annual grasses and broadleaf weeds and in large-scale on crops such as rice, celery and lettuce.

Earliest reports make use of phosgene as a starting material; however, this reagent is extremely toxic and hazardous to handle, especially in large quantities. Many reports illustrate the intramolecular rearrangement of various derivatives to afford S-alkyl thiocarbamates; however, these rearrangements are extremely limited in starting substrates. See Kwart, H.; Evans, E. R. *J. Org. Chem.* 1966, 31, 410–413; Newman, M. S.; Karmes, H. A. *J. Org. Chem.* 1966, 31, 3980–3984; Newman, M. S.; Hetzel, F. W. *J. Org. Chem.* 1969, 34, 3604–3606; Hackler, R. E.; Balko, T. W. *J. Org. Chem.* 1973, 38, 2106–2109, all of which are incorporated herein by reference. Similarly, transition metal catalysts containing elements such as palladium, nickel, and rhodium have also been employed to promote rearrangement and product formation. See Jones, W. D.; Reynolds, K. A.; Sperry, C. K.; Lachicotte, R. J.; Godleski, S. A.; Valente, R. R. *Organometallics* 2000, 19, 1661–1669; Kuniyasu, H.; Hiraike, H.; Morita, M.; Tanaka, A.; Sugoh, K.; Kurosawa, H. *J. Org. Chem.* 1999, 64, 7305–7308; Böhme, A.; Gais, H.-J. *Tetrahedron: Asymmetry* 1999, 10, 2511–2514; and Jacob, J.; Reynolds, K. A.; Jones, W. D.; Godleski, S. A.; Valente, R. R. *Organometallics* 2001, 20, 1028–1031, all of which are incorporated herein by reference. There are a variety of other known methods; however, most require the preparation of complex starting materials. See Batey, R. A.; Yoshina-Ishii, C.; Taylor, S. D.; Santhakumar, V. *Tetrahedron Lett.* 1999, 40, 2669–2672, incorporated herein by reference. Carbon monoxide and elemental sulfur are frequently employed in such preparation; however, these methods involve multi-step approaches, which incorporate metal catalysts, or proceed in low yields. The most widely used method for preparation of these compounds makes use of gaseous carbonyl sulfide (COS), which condenses with a secondary amine, followed by subsequent treatment with base and an alkyl halide. This three-step process is limited to secondary amines. See Reddy, T. I.; Bhawal, B. M.; Rajappa, S. *Tetrahedron Lett.* 1992, 33, 2857–2860, incorporated herein by reference.

Condensation of a thiol with an isocyanate affords the corresponding thiocarbamate; however, this route was only demonstrated when alkoxy and aroxysulfonyl isocyanates were employed. See Beji, M.; Sbihi, H.; Baklouti, A.; Cambon, A. *J. Fluorine Chem.* 1999, 99, 17–24, incorporated herein by reference. Moreover, the hydration of a variety of organic thiocyanates have been reported to afford the desired compound in the presence of hydrogen chloride; however, this method is limited to only N,N-unsubstituted thiocarbamates. See Zil'berman, E. N.; Lazaris, A. Y. *J. Gen. Chem. USSR* 1963, 33, 1012–1014, incorporated herein by reference. S-alkyl thiocarbamates have also been prepared from salts of dithiocarbamic acid, which are prepared by the addition of secondary amines to carbon disulfide ($CS_2$). See *Advanced Organic Chemistry* 5$^{th}$ Ed.; Smith, M. B.; March, J., Eds.; Wiley Interscience: New York, 2001; Chapter 16, incorporated herein by reference. Despite being a novel approach, this method is limited to N,N-disubstituted thiocarbamates. Although there are numerous variations, there lacks a simple comprehensive synthetic approach for the facile preparation of both N-substituted, N,N-disubstituted and N,N-unsubstituted S-alkylthiocarbamates.

SUMMARY OF THE INVENTION

It is the object of this invention to teach a new synthesis method for the preparation of S-alkylthiocarbamate and S-arylthiocarbamate compounds. This is a one-pot two-step general synthesis of thiocarbamate compounds having two routes to the same product compound depending on the order of reagent addition. In the preferred route, a precursor thiol reagent is first reacted with trichloroacetyl chloride to produce an isolatable S-alkyl or S-aryl trichloroacetyl thioester intermediate, which is then reacted with an amine to yield the corresponding thiocarbamate product. In the alternate route, the amine is first reacted with trichloroacetyl chloride to produce an isolatable trichloroacetamide intermediate, which is then reacted with the precursor thiol to yield the corresponding thiocarbamate product. This new method has the following features and advantages: (1) structural generality (i.e. aliphatic or aromatic thiol used in combination with ammonia, a primary or a secondary amine whose substituents may also be aromatic or aliphatic); (2) facile purification; (3) high isolated yields; (4) one-pot two-step simplified procedures; and (5) avoidance of toxic and environmentally objectionable reagents (e.g. phosgene, carbon monoxide, carbonyl sulfide, carbon disulphide).

DETAILED DESCRIPTION OF THE PREFERRED EMBODIMENTS

A method of preparing S-alkyl and S-aryl thiocarbamates according to a preferred embodiment of the present invention takes advantage of very facile chemistry involving adduct formation between trichloroacetyl chloride ($Cl_3COCl$) and a thiol (1) or an amine (4) followed by a very unique and unexpected chemistry involving nucleophilic displacement of the trichloromethyl moiety as chloroform to yield a variety of thiocarbamate products (3) with various substitutions ($R^1$, $R^2$ and $R^3$) on the sulfur and amine sites as illustrated in Scheme 1.

Scheme 1

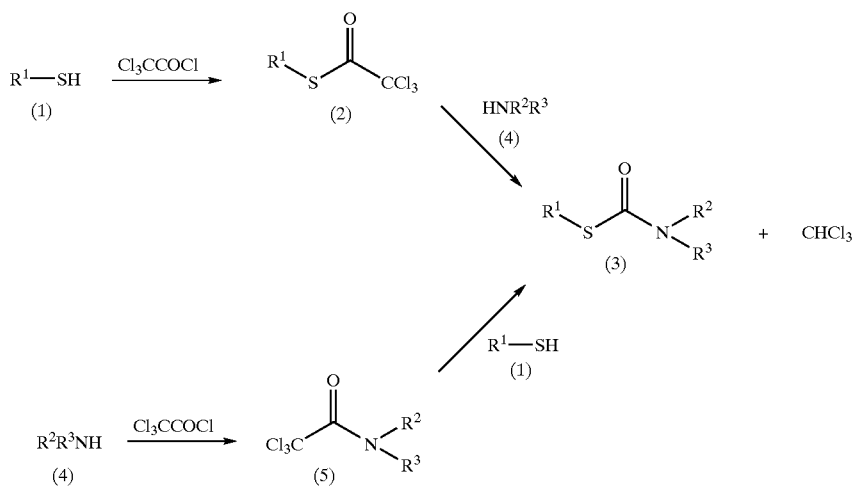

It is the unique and unexpected chemistry of the trichloroacetyl thioester adduct (2) and the trichloroacetamide adduct (5) that form the basis of this invention. These adducts undergo nucleophilic substitution reactions resulting, not in regeneration of the initial thiol or amine precursors as might be expected from the general behavior of esters and amides, but in displacement of the trichloromethyl group as chloroform and formation of the thiocarbamate product (3). As depicted in Scheme 1, these adducts serve as intermediate compounds in two complementary routes to the same product. In the upper route adduct 2 undergoes a nucleophilic displacement reaction with an amine reagent, while in the lower route adduct 5 undergoes a nucleophilic displacement reaction with a thiol. The identity of substituents $R^1$, $R^2$ and $R^3$ is determined by the selection of the thiol (1) and amine (4) reagents. This new chemistry provides for a preferred (1→2→3) route and an alternate route (4→5→3); the basis for the prefer route being the higher yield.

In the preferred route, the thiol-$Cl_3COCl$ adduct (2) is prepared by slow addition of an alkyl or aryl thiol to an excess of the $Cl_3COCl$ at 20° C. and stirred under dry atmosphere until adduct formation is complete. The molar excess of $Cl_3COCl$ may range from a factor of 1.05 to 10 with 2 being preferred. The adduct formation reaction is mildly exothermic and some external temperature control is advisable, although the temperature need not be rigorously maintained at 20° C. The formation of compound (2) proceeds rapidly without solvent, and the rate of consumption of the thiol is dependent on the thiol chemical structure in the general order of alkyl>benzyl>>phenyl. Reaction with the alkyl thiol is complete within about 15 minutes, whereas the benzyl thiol requires about 30 minutes and the phenyl derivative requires approximately 45 minutes to achieve complete conversion. The progress of the reaction is easily monitored by evolution of HCl gas or NMR analysis. Upon completion, the excess $Cl_3COCl$ and hydrochloric acid byproduct are readily evaporated or distilled at reduced pressure to yield the essentially pure thioester adduct (2). Although temperature and pressure conditions for evaporation or distillation are not crucial, the preferred temperature and pressure is 120° C. and 5 mmHg respectively. Examples of the S-thioester intermediate product are depicted in Table 1.

TABLE 1

Examples of Preparation of S-Thioester

| Example | Thiol (1) | S-Ester Product (2) |
|---------|-----------|---------------------|
| 1 | 1, $R^1$ = $nC_6H_{13}$ | 2, $R^1$ = $nC_6H_{13}$ |
| 2 | 1, $R^1$ = Ph | 2, $R^1$ = Ph |
| 3 | 1, $R^1$ = $pClPhCH_2$— | 2, $R^1$ = $pClPhCH_2$— |

The second step involves the displacement of the trichloromethyl group of the thioester adduct (2) as chloroform upon treatment with an amine (4) to afford the thiocarbamate product (3). This product may be synthesized with a variety of substituents from a single intermediate (2) by altering the amine employed. Amine reagents include ammonia, primary and secondary amines with aliphatic or aromatic substituents. The transformation of adduct (2) into product (3) is conducted in aqueous or organic media or without solvent depending on the solid or liquid nature and solubilities of the reagents and products. Typically, an excess of amine is added to the thioester adduct (2) in a liquid medium and reacted at a mildly elevated temperature (~60° C.) for several hours. The product (3) is isolated by concentration, distillation, recrystallization and/or chromatography. The molar excess of amine (4) may range from a factor of 1.1 to 10 with a factor of 2 being preferred. When used, solubilizing media may include water and organic solvents. When ammonia is the amine reactant, water is a particularly effective solvent. A solventless system works well when using liquid primary amines, and methanol works well when employing secondary amines. A variety of thiocarbamate products (3) with various substitutions on the sulfur $R^1$ and the amine $R^2$ and $R^3$ sites are prepared in this manner. Examples with aliphatic and aromatic substituents synthesized by this procedure are depicted in Table 2.

TABLE 2

Examples of Thiocarbamate Syntheses by the Preferred Route.

| Example | S-Ester | Amine | Product | Time (h) | Temp °C. | Yield (%) |
|---|---|---|---|---|---|---|
| 4 | 2, $R^1$ = $nC_6H_{13}$— | $NH_3$ | 3 $R^1$ = $nC_6H_{13}$, $R^2$ = $R^3$ = H | .25 | 20 | 100 |
| 5 | 2, $R^1$ = $nC_6H_{13}$— | $nBuNH_2$ | 3, $R^1$ = $nC_6H_{13}$, $R^2$ =H, $R^3$ = nBu | .25 | 20 | 87 |
| 6 | 2, $R^1$ = $nC_6H_{13}$— | $tBuNH_2$ | 3, $R^1$ =$nC_6H_{13}$, $R^2$ =H, $R^3$ = tBu | .25 | 20 | 83 |
| 7 | 2, $R^1$ = $nC_6H_{13}$— | $Et_2NH$ | 3, $R^1$ = $nC_6H_{13}$, $R^2$ = $R^3$ = Et | 1 | 20 | 94 |
| 8 | 2, $R^1$ = Ph— | $NH_3$ | 3, $R^1$ = Ph, $R^2$ = $R^3$ = H | 12 | 60 | 98 |
| 9 | 2, $R^1$ = Ph— | $Et_2NH$ | 3, $R^1$ = Ph, $R^2$ = $R^3$ = Et | 12 | 60 | 90 |
| 10 | 2, $R^1$ = $pClPhCH_2$— | $NH_3$ | 3, $R^1$ = $pClPhCH_2$— $R^2$ = $R^3$ = H | 4 | 60 | 99 |
| 11 | 2, $R^1$ = $pClPhCH_2$— | $Et_2NH$ | 3, $R^1$ = $pClPhCH_2$—, $R^2$ = $R^3$ = Et | 4 | 60 | 91 |

The alternate synthesis route in the lower part of Scheme 1 is simply a reversal in order of using the thiol and amine reagents. The trichloroacetamide adduct (5) is formed by the addition of an amine reagent (4) to an excess of $Cl^3COCl$ in an organic solvent at a reduced temperature. The molar excess of the $Cl_3COCl$ may range from a factor of 1.05 to 10 with a factor of 2 being preferred. Although the temperature is not critical, the optimum temperature is 0° C. to prevent ammonium salt formation with excess amine. Likewise, the amine selection is flexible to include those eligible for the preferred route. Also, the use of a solvent system facilitates control of the reaction rate and product formation. Purification of the amine-$Cl_3COCl$ adduct (5) may be performed by distillation. Treatment of the adduct (5) in a solution of tetahydrofuran or other suitable solvent at 20° C. with an excess of thiol (1) affords the corresponding compound (3) after heating at 100° C. for four hours. The excess may range from 1.05 to 10 equivalents with 1.5 being preferred. The temperature is not critical and both the addition and reaction can be performed at a wide range of temperatures with those reported being optimum for maximum yield. The product is isolated by extraction with an organic solvent and sequentially washed with water to remove any unreacted starting materials and byproducts. Additional purification was performed employing flash column chromatography to afford the desired product with yields reported in Table 3.

TABLE 3

Examples of Thiocarbamate Syntheses by the Alternate Route.

| Example | Thiol | Temp °C. | Time (h) | Product | Yield % |
|---|---|---|---|---|---|
| 13 | 1, $R^1$ = $nC_6H_{13}$ | 60 | 4 | 3, $R^1$ = $nC_6H_{13}$, $R^2$ = $R^3$ = Et | 59 |
| 14 | 1, $R^1$ = Ph | 100 | 8 | 3, $R^1$ = Ph, $R^2$ = $R^3$ = Et | 63 |
| 15 | 1, $R^1$ = $pClPhCH_2$— | 80 | 6 | 3, $R^1$ = $pClPhCH_2$—, $R^2$ = $R^3$ = Et | 54 |

Experimental Details

Methanol was distilled from calcium hydride under nitrogen. Moisture sensitive reactions were conducted in oven-dried glassware under a nitrogen atmosphere unless otherwise noted. Analytical thin-layer chromatography was performed on precoated silica gel sheets, and flash column chromatography was accomplished using silica gel, 60Å (200–400 mesh). $^1H$ and $^{13}C$ NMR spectra were taken in $CDCl_3$ at 300 and 75 MHz respectively, with a TMS internal standard. Chemical shifts are reported in units downfield from TMS. Coupling constants, J, are reportrd in units of Hertz (Hz).

EXAMPLE 1

Synthesis and purification of trichlorothioacetic acid S-hexyl ester ($2R^1$=$nC_6H_{13}$). Into a 25 mL round-bottomed flask equipped with magnetic stir bar and a drying tube was placed 3.08 g of trichloroacetyl chloride (16.92 mmol). To the stirred solution was dropwise added the thiol (1) (8.46 mmol) utilizing a syringe over a period of 15 min. The mildly exothermic reaction was allowed to stir for 2 h. Then, the drying tube was replaced by a short-path still head. The resulting reaction mixture was heated under reduced pressure (5 mmHg) to 120° C. while the excess unreacted reagents and byproducts were removed, thus purifying the product. The corresponding product was afforded in quantitative yields. FTIR: 2961, 2929, 2851, 1693, 1467, 1035, 857, 785, 750, 619 $cm^{-1}$; $^1H$ NMR: 3.04 (t, J=6, 2H), 2.68 (dt, 2H), 1.48–1.27 (m, 6H), 0.92 δ (t, J=6, 3H); $^{13}C$ NMR: 189.3, 94.9, 31.7, 31.2, 28.5, 28.4, 22.4, 13.9 δ; Bp 137° C. @1 Torr, (literature 104° C. @0.4 Torr; see Kuliev, A. M.; Zeinalova, G. A.; Kuliev, A. B.; Hasanov, M. S. *Neftekhimiya* 1971, 11, 906–910).

EXAMPLE 2

Synthesis and purification of trichlorothioacetic acid S-phenyl ester (2 $R^1$=Ph). The procedure was identical to that of Example 1, except relative reagent quantities were adjusted so that the stoichiometry was identical to that of Example 1. The product was obtained in quantitative yield. FTIR: 3420, 3061, 1705, 1479, 1447, 1095, 1023 $cm^{-1}$; $^1H$ NM 7.46–7.46 δ (m, 5H); $^{13}C$ NMR 187.7, 134.7, 130.5, 129.7, 129.4, 125.9 δ; Mp 55–57° C., (literature 53–55 Bp 115–118° C. @ 1 Torr; see Talley, J. J. *Synthesis*, 1981, 7, 549–549; Shchepin, V. V.; Efremov, D. I.; Desyatkov, D. A. *Russ. J. Org. Chem.* (*Eng.*) 1993, 29, 342; Ward, Jr., L. F.; Whetstone, R. R.; Pollard, G. E.; Phillips, D. D. *J. Org. Chem.* 1968, 33, 4470–4475).

EXAMPLE 3

Synthesis and purification of trichlorothioacetic acid S-(4-chlorobenzyl) ester (2 $R^1$=pClPhCH$_2$—). The procedure was identical to that of Example 1, except relative reagent quantities were adjusted so that the stoichiometry was identical to that of Example 1. The product was obtained in quantitative yield. FTIR: 3029, 2977, 2930, 1776, 1689, 1594, 1487, 1408, 1241, 1198, 1099, 1039, 1011, 852, 781, 745, 690 cm$^{-1}$; $^1$H NMR 7.31–7.25 (m, 4H), 4.18 δ (s, 2H); $^{13}$C NMR 188.5, 133.8, 133.6, 130.3, 129.1, 94.4, 35.3 δ. Anal. Calcd for C$_9$H$_6$Cl$_4$OS: C, 35.56; H, 1.99. Found: C, 35.89; H, 1.96.

EXAMPLE 4

Synthesis and purification of thiocarbamic acid S-hexyl ester (3 $R^1$=nC$_6$H$_{13}$, $R^2$=H, $R^3$=H). Into a 50 mL round-bottomed flask equipped with magnetic stir bar and a positive flow of nitrogen were placed trichloro-thioacetic ester (compound 2 $R^1$=nC$_6$H$_{13}$, 1.90 mmol) and 10 mL methanol. The solution was stirred at room temperature 5 min before the rapid addition of the corresponding amine (30%NH$_3$/H$_2$O, 3.80 mmol). The resulting solution was stirred rapidly at the respective temperature for 24 h (see Table 2). The product was isolated in quantitative yield by filtration and washing with water. FTIR (neat): 3366, 3326, 3247, 2971, 2943, 2589, 1653 cm$^{-1}$; $^1$H NMR 6.62 (bs, 1NH), 6.08 (bs, 1NH), 2.65 (t, J=7, 2H), 1.63–1.59 (m, 4H), 1.27–1.16 (m, 4H), 0.86 δ (t, J=7, 3H); $^{13}$C NMR 163.6, 39.2, 31.4, 29.2, 28.2, 22.2, 14.0 δ; Mp 99–102° C. (literature 105° C.; see Riemschneider, R. *Monatsh. Chem.* 1953, 84, 1228–1233).

EXAMPLE 5

Synthesis and purification of n-butylthiocarbamic acid S-hexyl ester (3, $R^1$=nC$_6$H$_{13}$, $R^2$=H, $R^3$=nBu). This compound was prepared from trichloro-thioacetic ester (compound 2 $R^1$=nC$_6$H)$_{13}$) and n-butylamine using a stoichiometry and a procedure identical to that of Example 4. The product was purified by recrystallization from ethanol and isolated in 87% yield. Spectroscopic data correlates with that previously reported in the literature. (see Kochansky, J.; Feldmesser, J. *Journal of Nematology* 1989, 21, 158–163) FTIR: 3308, 2958. 2926, 1651, 1523, 1463, 1463, 1372, 1150, 921 cm$^{-1}$, $^1$H NMR: 8.20 (bs, 1NH), 3.03 (t, J=6, 2H), 2.69 (t, J=6, 2H), 1.82–1.65 (m, 2H), 1.62–1.57 (m, 4H), 1.47–1.29 (m, 6H), 0.96 (t, J=6, 3H), 0.90 δ (t, J=6, 3H); $^{13}$C NMR: 164.3, 44.7, 39.5, 38.8, 30.9, 29.2, 27.9, 22.2, 19.5, 13.7, 13.2 δ; Mp 142–148° C. (dec).

EXAMPLE 6

Synthesis and purification of t-butylthiocarbamic acid S-hexyl ester (3, $R^1$=nC$_6$H$_{13}$, $R^2$=H, $R^3$=tBu). This compound was prepared from trichloro-thioacetic ester (compound 2 $R^1$=nC$_6$H$_{13}$) and t-butylamine using a stoichiometry and a procedure identical to that of Example 4. The product was purified by recrystallization from ethanol and isolated in 83% yield. FTIR (neat): 2958, 2922, 2858, 1667, 1450, 1265 cm$^{-1}$; $^1$H NMR: 5.80 (bs, 1NH), 2.268 (t, J=7, 2H), 1.77–1.54 (m, 4H), 1.40 (s, 9H), 1.32–1.29 (m, 4H), 0.89 δ (t, J=6, 3H); $^{13}$C NMR 163.0, 67.0, 52.4, 39.1, 31.4, 31.3, 29.0, 22.7, 14.0 δ; Mp 212–124° C.; Anal. Calcd for C$_{11}$H$_{23}$NOS: C, 60.78; H, 10.66; N, 6.44. Found: C, 60.84; H, 10.37; N, 6.79.

EXAMPLE 7

Synthesis and purification of diethylthiocarbamic acid S-hexyl ester (3, $R^1$=nC$_6$H$_{13}$, $R^2$=Et, $R^3$=Et). This compound was prepared from trichloro-thioacetic ester (compound 2 $R^1$=nC$_6$H$_{13}$) and diethylamine using a stoichiometry and a procedure identical to that of Example 4. The product was purified by recrystallization from methanol and isolated in 94% yield. FTIR: 2969, 2819, 2794, 1646, 1487, 1372, 1205, 1094, 1011 cm$^{-1}$, $^1$H NMR: 3.05 (q, J=6, 4H), 2.68 (t, J=6, 2H), 1.70–1.48 (m, 2H), 1.43 (t, J=6, 6H), 1.41–1.35 (M, 2H), 1.30–1.15 (m, 4H), 0.89 δ (t, J=6, 3H); $^{13}$C NMR: 162.7, 42.1, 38.5, 30.8, 28.7, 27.8, 22.1, 13.8, 12.1 δ; Mp 64–66° C.; Anal. Calcd for C$_{11}$H$_{23}$NOS: C, 60.78; H, 10.66; N, 6.44. Found: C, 60.98; H, 10.36; N, 6.68.

EXAMPLE 8

Synthesis and purification of thiocarbamic acid S-phenyl ester (3, $R^1$=Ph, $R^2$=H, $R^3$=H). This compound was prepared from trichloro-thioacetic ester (compound 2 $R^1$=Ph) and NH$_3$/H$_2$O using a stoichiometry and a procedure identical to that of Example 4. The product was purified by flash chromatography on a silica column with hexane/ethyl acetate elution and isolated in 98% yield. FTIR: 3648, 3623, 3068, 2984, 1687, 1574, 1475, 1435, 1071, 1019 cm$^{-1}$; $^1$H NMR (acetone-d$_6$): 9.97 (bs, 2NH), 7.51 (d, J=6, 2H), 7.36 (t, J=6, 2H), 7.23 δ (d, J=7, 1H); $^{13}$C NMR (acetone-d$_6$): 176.3, 128.9, 127.3, 127.0, 127.0, 126.8 δ; Mp 98–100° C. (literature 96–98° C.; see Lewis, E. S.; Cooper, J. E. *J. Am. Chem. Soc.* 1962, 84, 3847–3852; Riemschneider,. R.; Wojahn, F.; Orlick, G. *J. Am. Chem. Soc.* 1951, 73, 5905–5907).

EXAMPLE 9

Synthesis and purification of diethylthiocarbamic acid S-phenyl ester (3, $R^1$=Ph, $R^2$=Et, $R^3$=Et). This compound was prepared from trichloro-thioacetic ester (compound 2 $R^1$=Ph) and diethylamine using a stoichiometry and a procedure identical to that of Example 4. The product was purified by flash chromatography on a silica column with hexane/ethyl acetate elution and isolated in 90% yield. Spectroscopic data correlates with that previously reported in the literature. (see Mizuno, T.; Nishiguchi, I.; Hirashima, T. *Tetrahedron* 1993, 49, 2403–2412) FTIR: 2973, 2819, 2775, 2482, 2391, 1657, 1483, 1360, 1210, 1063 cm$^{-1}$; $^1$H NMR 9.39 (bs, 1NH), 7.43 (d, J=6, 2H), 7.27–7.22 (m, 3H), 2.97 (q, J=6, 4H), 1.38 δ (t, J=6, 6H); $^{13}$C NMR 168.7, 133.2, 130.3, 128.9, 128.1, 42.20, 11.1 δ; Mp 46–49° C.

EXAMPLE 10

Synthesis and purification of thiocarbamic acid S-(4-chlorobenzyl) ester (3, $R^1$=pClPhCH$_2$—, $R^2$=H, $R^3$=H). This compound was prepared from trichloro-thioacetic ester (compound 2 $R^1$=pClPhCH$_2$—) and NH$_3$/H$_2$O using a stoichiometry and a procedure identical to that of Example 4. The product was purified by flash chromatography on a silica column with hexane/ethyl acetate elution and isolated in 99% yield. FRIR: 3176, 3025, 1657, 1486, 1408, 1328, 1091, 329 cm$^{-1}$; $^1$H NMR 7.89 (bs, 2NH), 7.41 (d, J=7, 2H), 7.33 (d, J=7, 2H), 3.78 δ (s, 2H); $^{13}$C NMR: 205.4, 135.3, 131.9, 129.9, 127.5, 40.8 δ; Mp 130–133° C., (literature 137–139° C.; see Ishikawa, K.; Okuda, I.; Kuwatsuka, S. *Agric. Biol. Chem.* 1973, 37, 165–173).

EXAMPLE 11

Synthesis and purification of diethylthiocarbamic acid S-(4-chlorobenzyl) ester (3, $R^1$=pClPhCH$_2$—, $R^2$=Et, $R^3$=Et). This compound was prepared from trichlorothioacetic ester (compound 2 $R^1$=pClPhCH$_2$—) and diethylamine using a stoichiometry and a procedure identical to that of Example 4. The product was purified by flash chromatography on a silica column with hexane/ethyl acetate elution and isolated in 91% yield. The procedure was identical to that of Example 4, except relative quantities were adjusted so that a stoichiometric relationship was identical to that of Example 4. Spectroscopic data correlates with that previously reported in the literature. (see Kodama, S.; Yamamoto, A.; Matsunaga, A. J. *Agric. Food. Chem.* 1997, 45, 990–994; Mizuno, T.; Nishiguchi, I.; Sonoda, N. *Tetrahedron* 1994, 50, 5669–5680) FTIR: 3017, 2977, 2819, 1657, 1491, 1368, 1206, 1091, 1015 cm$^{-1}$; $^1$H NMR: 7.28 (d, J=6, 2H), 7.15 (d, J=6, 2H), 3.67 (s, 2H), 3.07 (q, J=6, 4H), 1.40 δ (t, J=6, 6H); $^{13}$C NMR: 168.0, 134.8, 131.7, 129.6, 127.3, 42.1, 36.3, 10.2 δ; Bp. 161–164° C. /2 torr.

EXAMPLE 12

Synthesis and purification of 2,2,2-trichloro-N,N-diethyl-acetamide (5, $R^2$=$R^3$=Et). Into a 50 mL two-necked round-bottomed flask equipped with a positive flow of $N_2$ a condenser and a septa, were placed methanol (20 mL) and diethylamine (1.00 g, 13.67 mmol). The resulting solution was cooled in an ice bath to 0° C. and allowed to stir at room temperature for 10 min. before the dropwise addition of trichloroacetyl chloride (4.97 g, 27.34 mmol) employing a syringe over a 45 min period. Distillation of unreacted amine and trichloroacetyl chloride was performed using a short path still head. The reaction mixture was diluted with CH$_2$Cl$_2$ (30 mL) and washed with water (3×10 mL). The organic layer was dried over MgSO$_4$ and concentrated under reduced pressure to afford the crude product, which was subsequently purified employing flash column chromatography resulting in the desired product (5) in a 45% yield. FRIR: 2989, 2937, 1708, 1519, 1455, 1364, 1268, 12114, 912, 821, 733, 682 cm$^{-1}$; $^1$H NMR: 3.77 (q, J=6, 4H), 1.15 δ (t, J=6, 6H); $^{13}$C NMR: 160.3, 93.1, 52.8, 25.4 δ.

EXAMPLE 13

Synthesis and purification of diethylthiocarbamic acid S-hexyl ester (3, $R^1$=nC$_6$H$_{13}$, $R^2$=Et, $R^3$=Et). Into a 50 mL round-bottomed flask was placed 1.00 g (4.58 mmol) compound 5 ($R^2$=$R^3$=Et) and 15 mL of freshly distilled THF. This solution stirred at room temperature for 15 min before the subsequent addition of thiol (1, $R^1$=nC$_6$H$_{13}$) (6.86 mmol). The resulting solution was gently refluxed for 4 hours and stirred at 20 overnight. Reaction mixture was diluted with CH$_2$Cl$_2$ (30 mL) and washed with water (3×10 nL). The organic layer was dried over MgSO$_4$ and concentrated under reduced pressure to afford a brown oil. Subsequent purification employing flash column chromatography to afford the desired product in 59% yield.

EXAMPLE 14

Synthesis and purification of diethylthiocarbamic acid S-phenyl ester (3, $R^1$=Ph, $R^2$=Et, $R^3$=Et). Into a 50 mL round-bottomed flask was placed 1.00 g (4.58 mmol) compound 5 ($R^2$=$R^3$=Et) and 15 mL of freshly distilled THF. This solution stirred at room temperature for 15 min before the subsequent addition of thiol (1, $R^1$=Ph) (6.86 mmol). The resulting solution was gently refluxed for 4 hours and stir at 20 overnight. Reaction mixture was diluted with CH$_2$Cl$_2$ (30 mL) and washed with water (3×10 mL). The organic layer was dried over MgSO$_4$ and concentrated under reduced pressure to afford a brown oil. Subsequent purification employing flash column chromatography to afford the desired product in 63% yield.

EXAMPLE 15

Synthesis and purification of thiocarbamic acid S-(4-chlorobenzyl) ester (3, $R^1$=pClPhCH$_2$—, $R^2$=H, $R^3$=H). Into a 50 niL round-bottomed flask was placed 1.00 g (4.58 mmol) compound 5 ($R^2$=$R^3$=Et) and 15 mL of freshly distilled THF. This solution stirred at room temperature for 15 min before the subsequent addition of thiol (1, $R^1$=pClPhCH$_2$—) (6.86 mmol). The resulting solution was gently refluxed for 4 hours and stir at 20 overnight. Reaction mixture was diluted with CH$_2$Cl$_2$ (30 mL) and washed with water (3×10 mL). The organic layer was dried over MgSO$_4$ and concentrated under reduced pressure to afford a brown oil. Subsequent purification employing flash column chromatography to afford the desired product in 54% yield.

The above description is that of a preferred embodiment of the invention. Various modifications and variations are possible in light of the above teachings. It is therefore to be understood that, within the scope of the appended claims, the invention may be practiced otherwise than as specifically described. Any reference to claim elements in the singular, e.g. using the articles "a," "an," "the," or "said" is not construed as limiting the element to the singular.

What is claimed:

1. A method for preparing S-alkyl and S-aryl thiocarbamates, comprising the steps of:
   (a) reacting a thiol with trichloroacetyl chloride to create a trichloroacetyl thioester adduct; and
   (b) reacting the trichloroacetyl thioester adduct with an amine to create the thiocarbamate.

2. The method of claim 1 wherein the thiol is an alkyl or an aryl thiol.

3. The method of claim 1 wherein in step (a) there is a molar excess of trichloroacetyl chloride with a factor in the range of 1.05 to 10.

4. The method of claim 1 wherein the reaction of step (a) occurs at about 20° C.

5. The method of claim 1 wherein in step (a) excess trichloroacetyl chloride and any byproducts are evaporated or distilled.

6. The method of claim 1 wherein in step (b) there is a molar excess of amine with a factor in the range of 1.1 to 10.

7. The method of claim 1 wherein the reaction of step (b) occurs at about 60° C.

8. The method of claim 1 wherein water or an organic solvent is added in step (b).

9. The method of claim 1 wherein the thiocarbamate is isolated by concentration, distillation, recrystallization, chromatography, extraction or combinations thereof.

10. A method for preparing S-alkyl and S-aryl thiocarbamates, comprising the steps of:
    (a) reacting an amine with trichloroacetyl chloride to create a trichloroacetamide adduct; and
    (b) reacting the trichloroacetamide adduct with a thiol to create the thiocarbamate.

11. The method of claim 10 wherein the thiol is an alkyl or an aryl thiol.

12. The method of claim 10 wherein in step (a) there is a molar excess of trichloroacetyl chloride with a factor in the range of 1.05 to 10.

13. The method of claim 10 wherein the reaction of step (a) occurs at about 0° C.

14. The method of claim 10 wherein in step (a) excess trichloroacetyl chloride and any byproducts are distilled.

15. The method of claim 10 wherein in step (b) there is a molar excess of the thiol with a factor in the range of 1.05 to 10.

16. The method of claim 10 wherein an organic solvent is added in step (b).

17. The method of claim 16 wherein the organic solvent is tetrahydrofuran.

18. The method of claim 10 wherein the reaction of step (b) occurs at about 20° C. and the mixture is heated to about 100° C.

19. The method of claim 10 wherein the thiocarbamate is isolated by extraction with an organic solvent and washed with water.

20. The method of claim 10 wherein the thiocarbamate is purified by using flash column chromatography.

* * * * *